United States Patent [19]

Tlapek et al.

[11] Patent Number: 4,895,170
[45] Date of Patent: Jan. 23, 1990

[54] METHOD OF CONTRACEPTION USING DISPOSABLE CERVICAL CAP

[75] Inventors: Janet M. Tlapek, Saranac, Mich.; Margaret D. Tlapek, Prairie Village, Kans.

[73] Assignee: Page Hanes, Inc., Saranac, Mich.

[21] Appl. No.: 223,876

[22] Filed: Jul. 25, 1988

Related U.S. Application Data

[62] Division of Ser. No. 78,253, Jul. 20, 1987, Pat. No. 4,785,804.

[51] Int. Cl.$^4$ ............ A61B 17/00; A61F 5/00
[52] U.S. Cl. .................. 128/832; 128/837; 128/841
[58] Field of Search .............. 128/127-131, 128/830-841

[56] References Cited

U.S. PATENT DOCUMENTS

| | | | |
|---|---|---|---|
| 2,079,022 | 6/1935 | Martin | 128/837 |
| 2,141,040 | 3/1937 | Holt | 128/837 |
| 2,324,656 | 7/1943 | Vincent | 128/127 |
| 2,423,356 | 6/1947 | Waterbury | 128/837 |
| 2,818,856 | 1/1958 | Kohl | 128/838 |
| 2,836,177 | 2/1956 | Sells | 128/837 |
| 3,371,664 | 3/1968 | Pleshette | 128/127 |
| 3,952,737 | 4/1976 | Lipfert et al. | 128/127 |
| 4,198,965 | 4/1980 | Strickman et al. | 128/127 |
| 4,200,090 | 4/1980 | Drobish | 128/127 |
| 4,300,544 | 11/1981 | Rudel | 128/127 |
| 4,302,751 | 3/1982 | Loeb | 340/763 |
| 4,304,226 | 12/1981 | Drobish et al. | 128/127 |
| 4,381,771 | 5/1983 | Gabbay | 128/129 |
| 4,401,534 | 8/1983 | Goepp et al. | 128/131 |
| 4,630,602 | 12/1986 | Strickman et al. | 128/127 |
| 4,703,752 | 11/1987 | Gabbay | 128/131 |

FOREIGN PATENT DOCUMENTS 5471 1/1933 Australia .

Primary Examiner—Mickey Yu
Assistant Examiner—Michael Brown
Attorney, Agent, or Firm—Harness, Dickey & Pierce

[57] ABSTRACT

A disposable cervical cap has a thin, form-assuming pliable dome with an integrally-molded resilient retaining rim. The rim has a bevelled outer shoulder and contains an annular groove on its inner surface. The inner groove and rim define two ascending lips on the inner surface of the rim which prevent dislodgement of the cap from the cervix. The cervial cap includes a set of tabs on its outer surface to assist in positioning and placement of the cap and further includes a loop for removing the cap after use.

9 Claims, 1 Drawing Sheet

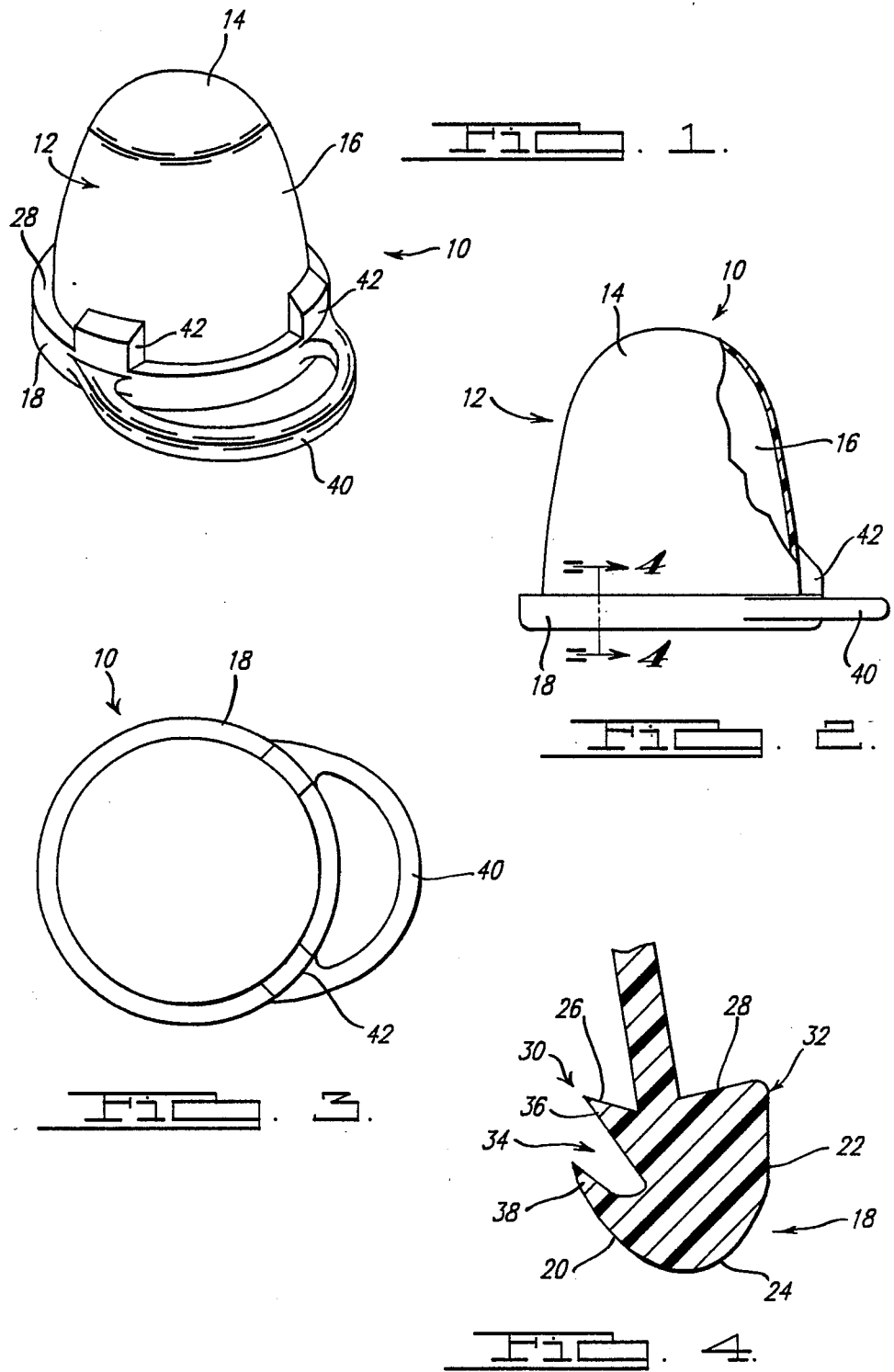

METHOD OF CONTRACEPTION USING DISPOSABLE CERVICAL CAP

This is a division of U.S. patent application Ser. No. 078,253, filed July 20, 1987 now U.S. Pat. No. 4,785,804.

BACKGROUND OF THE INVENTION

The present invention relates generally to contraceptive devices for females and, more particularly, to cervical caps which fit over the cervix to prevent semen from entering the cervical canal.

Recent disenchantment with contraceptive pills and intrauterine devices has led to a resurgence of interest in alternative means of birth control. One such alternative is the cervical cap which is positioned over the cervix to act as a sperm barrier. However, even through cervical caps are an effective means of contraception, the caps which are currently available are reusable caps which have several disadvantages.

Reusable cervical caps usually consist of a preformed sperm-impermeable rubber cap. These cervical caps are relatively thick-walled, semi-rigid devices which can be difficult to fit and place and rely primarily on suction to stay in position. As a result, reusable caps are usually manufactured in several sizes so they can be fitted to the individual. However, due to their rigidity, even properly-fitted caps can become dislodged during coitus or other activities, lose their suction grip on the cervix and allow sperm to enter the cervical canal.

Reusable cervical caps, which may be left in place for extended periods of time, must also allow for natural discharge from the cervix. Thus, the caps must be periodically removed from the cervix, or, alternatively, must be valved to permit emission of discharge while in place over the cervix. Cervical caps with valves, however, have lower contraceptive reliability because of potential access for sperm through the valve.

Reusable cervical caps also require proper cleaning and storage when not in use. Moreover, since reusable caps are usually made of rubber, they eventually deteriorate, thus further reducing their contraceptive reliability.

The present invention provides an improved disposable cervical cap which overcomes the aforementioned problems. Due to its novel contruction, the cervical cap of the present invention minimizes the chance of displacement of the cap from the cervix. Moreover, a single size of the cervical cap of the present invention will fit a majority of the female population.

SUMMARY OF THE INVENTION

The present invention provides a pre-fabricated disposable cervical cap having a thin-walled, flexible, and pliant dome with an integrally-molded flexible retaining rim. In position, the flexible dome of the cervical cap conforms to the exocervical surface to closely fit the cervix upon contact. Due to its thinness and pliability, the dome of the cap will continue to adhere to the surface of the cervix until removed. Adherence of the dome to the cervix is further facilitated by the moist cervical surface.

The cervical cap of the present invention is also kept in position by the novel rim construction of the cap. The inner surface of the rim includes an annular groove, the rim and groove defining upper and lower ascending rim lips. With the cap in position, the rim lips serve to grip the exocervical surface and keep the cap firmly in place. The dome thinness and rim construction of the cap thus eliminate the need for individual fittings for a large percent of the female population, reduce sperm access to the cervix and minimize the chance of dislodgement of the cap from its position.

The cervical cap of the present invention also has features to facilitate manual insertion and positioning over the cervix. Tabs located and integral with the outer surface of the cap permit placement of the cap with one finger and also aid in manipulating the device once positioned over the cervix to ensure a proper seal. Proper placement is further facilitated by the bevelled outer shoulder of the rim of the cap. The cervical cap of the present invention also includes a loop integral with the external surface of the cap to provide for easy and quick removal of the cap from the body.

To reduce the risk of infection from reuse, the cervical cap of the present invention is intended to be disposed after a single use. Since the cap is disposable, cleaning, storage, and deterioration problems of reusable caps are also eliminated.

These and further advantages of the cervical cap of the present invention will become apparent upon a further reading of the detailed description of the preferred embodiment taken in conjunction with the drawings.

BRIEF DESCRIPTION OF THE DRAWINGS

FIG. 1 is a perspective view of the of a preferred embodiment of the cervical cap of the present invention;

FIG. 2 is a side view, with a portion broken away and in section, of the cervical cap of FIG. 1;

FIG. 3 is a top elevational view of the cervical cap of FIG. 1;

FIG. 4 is a sectional view, broken away, taken along line 4-4 of a portion of the cervical cap of FIG. 2, particularly illustrating the construction of the retaining rim.

DETAILED DESCRIPTION OF THE PREFERRED EMBODIMENT

Referring to FIGS. 1—4, a preferred embodiment of a cervical cap of the present invention is illustrated and indicated generally by the numeral 10. Generally speaking, cervical cap 10 comprises a thin flexible dome 12, an apex portion 14 and base portion 16, and a retaining rim 18. Base portion 16 is integrally-molded with the flexible, resilient retaining rim 18. Dome 12 is generally thimble-shaped, with base portion 16 tapering inwardly toward apex portion 14. The outer diameter of rim 18 is greater than that of base portion 16 of dome 12.

Referring particularly to FIG. 4, retaining rim 18 has inner surface 20 and outer surface 22, bottom surface 24, and upper surfaces 26 and 28. Upper surface 26 extends leftward from base portion 16, as viewed in FIG. 4, and terminates at inner edge 30. Upper surface 28 extends upward from base portion 16, as viewed in FIG. 4, and terminates at outer shoulder 32. Upper surface 28 extends at an acute angle from adjacent base portion 16, preferably, for example, at about an 85 degree angle.

Retaining rim 18 has generally inwardly directed annular groove 34. The side walls of annular groove 34 extend generally toward bottom surface 24 with the opening of annular groove 34 facing inwardly and upwardly as shown in FIG. 4. Adjacent to annular groove 34 are annular upper rim lip 36 and annular lower rim lip 38. As illustrated in FIG. 4, both upper rim lip 36 and lower rim lip 38 extend generally inwardly and upwardly at an angle acute to dome base portion 16. This lip configuration serves to grip the cervix wall and helps keep the cervical cap in position over the cervix.

Referring again to FIGS. 1-3, cervical cap 10 includes a loop 40 integrally-molded to rim 18 and extending outwardly from outer surface 22. Loop 40 is used for removal of the cap from the body. Although it is preferred that the cap's removing means be an integrally-molded loop, it should be appreciated that a string, ring, tab or any other suitable appendage or device may be employed in its stead.

Cervical cap 10 further includes a set of projections or tabs 42 on its external surface to aid manipulating cap 10 for positioning and sealing the cap over the cervix. The tabs 42, usually two in number, are preferably integrally-molded to upper surface 28 of rim 18 and to dome base portion 16.

It is preferred that cervical cap 10 of the present invention be constructed of a sperm-impermeable, tear-resistant medical elastomer such as silicone rubber and formed by liquid injection modling. Other suitable materials, such as RTV thermoplastic thin enough to be form-conforming and pliant may also be employed.

Examples of suitable dimensions of cap 10 are as follows, it being understood that the exact dimensions can be varied to some extent. The thickness of dome 12 from apex to base may be, for example, from about 0.005 to about 0.007 inches thick at apex and about 0.0468 inches thick at base. Alternatively, but less preferably, the thickness of dome 12 may be uniform from apex to base, for example, in the range of from about 0.05 to about 0.001 inches. The height of dome 12 may be, for example, about 1.250 inches. The diameter of dome 12 at the lowest part of base portion 16 is suitably, for example, 1.275 inches. As noted above, the external diameter of retaining rim 18 is greater than that of dome base 16, and can be, for example, 1.465 inches in diameter. The height of retaining rim 18 is suitably, for example, about 0.1718 inches from outer shoulder 32 to the general plane of bottom surface 24.

In use, when cervical cap 10 of the present invention is inserted for positioning over the cervix, the bevelled outer top surface 28 of rim 18 assists in placement of cap 10 over the cervix. The tabs 42 of cap 10 further facilitate placement of cap 10 and aid in manipulating cap 10 after placement over the cervix, e.g. facilitating turning of the cap, to ensure a proper seal. When cervical cap 10 is in position, thin, pliable, form-assuming dome 12 of the cap conforms to the exocervical surface to help prevent dislodgement of the cap from its position over the cervix. After use, cervical cap 10 can easily be removed by grasping loop 40 and pulling the cap from the body.

Although not generally necessary, to increase its contraceptive effect, cervical cap 10 of the present invention can be pre-treated by coating or impregnating its surface with spermicidal agents during manufacture. Suitable spermicidal agents are, for example, nonoxyl-9 and oxynol-9. Cervical cap 10 which has not been so pre-treated during manufacture can, of course, be treated just prior to use by coating and/or filling the cap with commercially available spermicidal foams, gels or creams. Moreover, cervical cap 10 of the present invention can also be used in conjunction with spermicidal agents which can be inserted in the vaginal canal after placement of the cap over the cervix.

It will be appreciated that the above-disclosed embodiment is well calculated to achieve the objectives of the present invention. However, it is evident that those skilled in the art, once given the benefit of the foregoing disclosure, may make modifications of the specific embodiment described herein without departing from the spirit of the present invention. Such modifications are to be considered within the scope of the present invention which is solely limited by the scope and spirit of the appended claims.

What is claimed is:

1. A method of contraception for a female, comprising the steps of:
    inserting a cervical cap having an inner and outer surface into the vagina, said cervical cap comprising a form-assuming, non-resilient dome having an apex and base portion, and further comprising a flexible rim integrally-molded to said dome, said rim including an inner and outer surface and a bottom surface and, further having an annular groove descending acutely from said inner wall toward said bottom surface of said rim, whereby said inner wall and groove define an ascending lip on said inner wall;
    positioning said dome over the opening of the cervix;
    positioning said flexible rim over the cervix;
    positioning said ascending lip defined by said annular groove of said rim to provide intimate gripping contact of said ascending lip with the cervix wall; and
    manipulating said flexible rim to form a seal between said ascending lip and the cervix wall.

2. The method of claim 1, wherein said method further includes the step of manipulating said cap while positioned over the cervix to form a seal with the cervix.

3. The method of claim 2, wherein said insertion and said manipulation are performed manually.

4. The method of claim 1, wherein said method further includes the step of treating said cap with a spermicidal agent prior to insertion of said cap.

5. The method of claim 1, wherein said outer wall of said rim further includes a bevelled outer shoulder.

6. The method of claim 1, wherein said cap further includes a tab integrally-molded to said rim.

7. The method of claim 1, wherein said cap further includes a loop integrally-molded to said rim.

8. The method of claim 1, wherein said cap is formed of silicone rubber.

9. The method of claim 1, wherein said method further comprises the step of removing said cap from the cervix.

* * * * *

UNITED STATES PATENT AND TRADEMARK OFFICE
CERTIFICATE OF CORRECTION

PATENT NO. : 4,895,170

DATED : January 23, 1990

INVENTOR(S) : Janet M. Tlapek & Margaret D. Tlapek

It is certified that error appears in the above-identified patent and that said Letters Patent is hereby corrected as shown below:

Column 1, line 46, "contruction" should be --construction--.

Column 2, line 28, after "view" delete --of the--.

Column 3, line 20, "modling" should be --molding--.

Column 3, line 48, after "exocervical" insert --surface to closely fit and "cling" to the cervix. Upper rim lip 36 and lower rim lip 38 of retaining rim 18 also sealingly grip the exocervical--.

Signed and Sealed this

Thirtieth Day of April, 1991

Attest:

HARRY F. MANBECK, JR.

Attesting Officer

Commissioner of Patents and Trademarks